United States Patent
Ty et al.

(10) Patent No.: US 10,085,855 B2
(45) Date of Patent: Oct. 2, 2018

(54) SURGICAL INSTRUMENT FOR IMPLANT INSERTION

(71) Applicant: Beacon Biomedical, LLC, Jupiter, FL (US)

(72) Inventors: Dennis Ty, Jupiter, FL (US); Dale Mitchell, Jupiter, FL (US)

(73) Assignee: Beacon Biomedical, LLC, Jupiter, FL (US)

( * ) Notice: Subject to any disclaimer, the term of this patent is extended or adjusted under 35 U.S.C. 154(b) by 0 days.

(21) Appl. No.: 15/283,083

(22) Filed: Sep. 30, 2016

(65) Prior Publication Data

US 2017/0112635 A1    Apr. 27, 2017

Related U.S. Application Data

(60) Continuation-in-part of application No. 15/186,996, filed on Jun. 20, 2016, which is a division of application No. 14/153,768, filed on Jan. 13, 2014, now Pat. No. 9,370,384, which is a continuation of application No. 13/107,189, filed on May 13, 2011, now Pat. No. 8,628,535.

(60) Provisional application No. 62/235,085, filed on Sep. 30, 2015, provisional application No. 61/334,643, filed on May 14, 2010.

(51) Int. Cl.
*A61B 17/70* (2006.01)
*A61F 2/44* (2006.01)
*A61F 2/46* (2006.01)

(52) U.S. Cl.
CPC .......... *A61F 2/4611* (2013.01); *A61F 2/4465* (2013.01); *A61F 2002/4475* (2013.01); *A61F 2002/4623* (2013.01); *A61F 2002/4625* (2013.01); *A61F 2002/4679* (2013.01)

(58) Field of Classification Search
CPC .................. A61F 2/4611; A61F 2/4465; A61F 2002/4475; A61F 2002/4623; A61F 2002/4625; A61F 2002/4679; A61F 2002/2817; A61F 2002/30133; A61F 2002/30538; A61F 2002/30841; A61F 2002/30892; A61F 2002/4627; A61F 2002/30785; A61F 2230/0015; A61F 2250/0006
USPC .......... 606/90, 99, 96, 205–207, 264, 86 A; 623/17.11–17.16
See application file for complete search history.

(56) References Cited

U.S. PATENT DOCUMENTS

| | | |
|---|---|---|
| 6,530,929 B1 | 3/2003 | Justis et al. |
| 7,066,937 B2 | 6/2006 | Shluzas |
| 7,188,626 B2 | 3/2007 | Foley et al. |
| 7,520,879 B2 | 4/2009 | Justis et al. |
| 7,758,617 B2 | 7/2010 | Iott et al. |

(Continued)

FOREIGN PATENT DOCUMENTS

| | | |
|---|---|---|
| EP | 1221901 | 2/2007 |
| WO | WO20070857516 | 8/2007 |

*Primary Examiner* — Pedro Philogene
(74) *Attorney, Agent, or Firm* — McHale & Slavin, P.A.

(57) ABSTRACT

The present invention provides an orthopedic surgical tool for moving an implant to a surgical sight and installing the implant. The tool allows the surgeon the ability to navigate the implant through a surgical tube, then rotate the implant after reaching the sight and effect installation of the implant, and then effect its release from the tool. The implant can be rotated at any time during its installation within the constraints of other surgical devices.

16 Claims, 22 Drawing Sheets

(56) References Cited

U.S. PATENT DOCUMENTS

| | | |
|---|---|---|
| 7,892,239 B2 | 2/2011 | Warnick et al. |
| 8,043,293 B2 | 10/2011 | Warnick |
| 8,157,845 B2 | 4/2012 | Warnick |
| 8,231,633 B2 * | 7/2012 | Lim ................ A61F 2/4465 606/99 |
| 8,444,650 B2 * | 5/2013 | Warnick ............ A61F 2/4465 606/86 A |
| 8,628,535 B2 | 1/2014 | Mitchell et al. |
| D722,698 S | 2/2015 | Frankel et al. |
| 9,220,607 B2 * | 12/2015 | Palmatier ........... A61F 2/4611 |
| 9,345,586 B2 * | 5/2016 | Hunt ............... A61B 17/1659 |
| 9,615,939 B2 * | 4/2017 | Cho ................. A61F 2/4611 |
| 2005/0277934 A1 | 12/2005 | Vardiman |
| 2006/0247630 A1 | 11/2006 | Iott et al. |
| 2007/0078460 A1 | 4/2007 | Frigg et al. |
| 2007/0225808 A1 * | 9/2007 | Warnick ............ A61F 2/4465 623/17.11 |
| 2008/0009880 A1 | 1/2008 | Warnick et al. |
| 2008/0045956 A1 | 2/2008 | Songer et al. |
| 2008/0077138 A1 | 3/2008 | Cohen et al. |
| 2009/0264930 A1 * | 10/2009 | McBride ........... A61B 17/7004 606/250 |

* cited by examiner

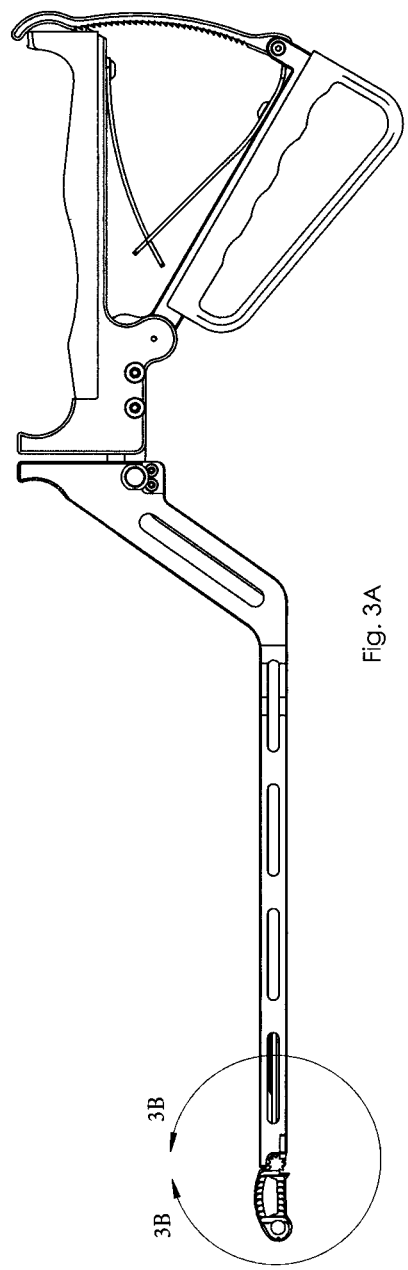

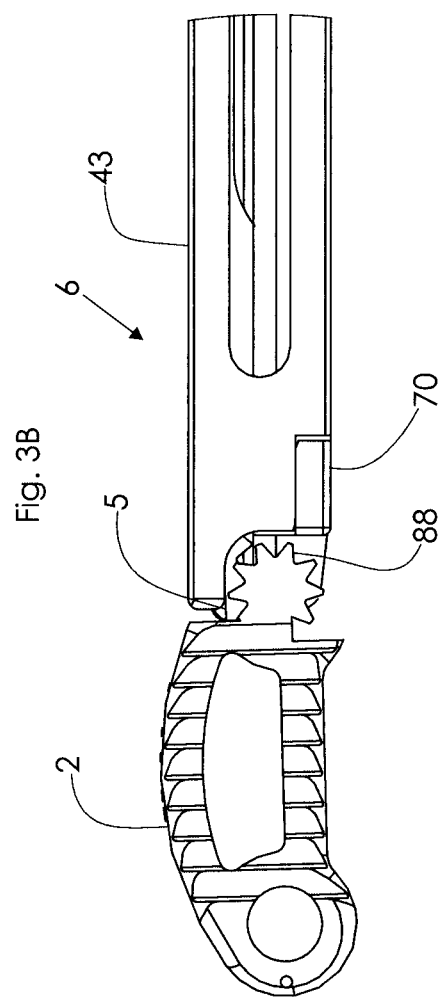

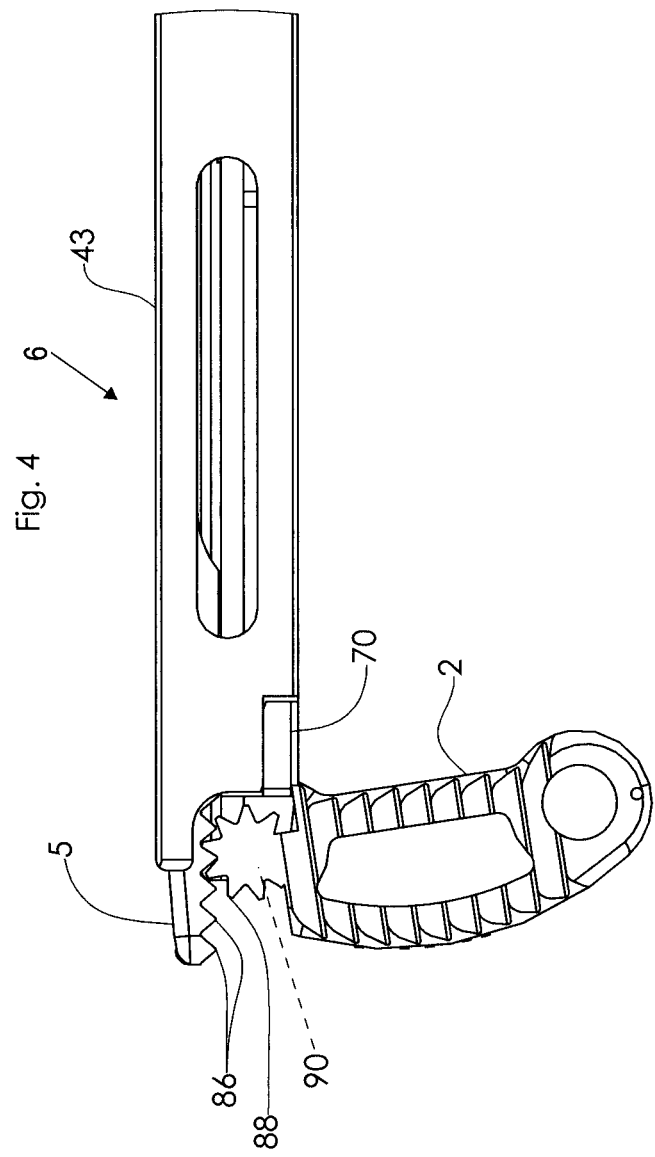

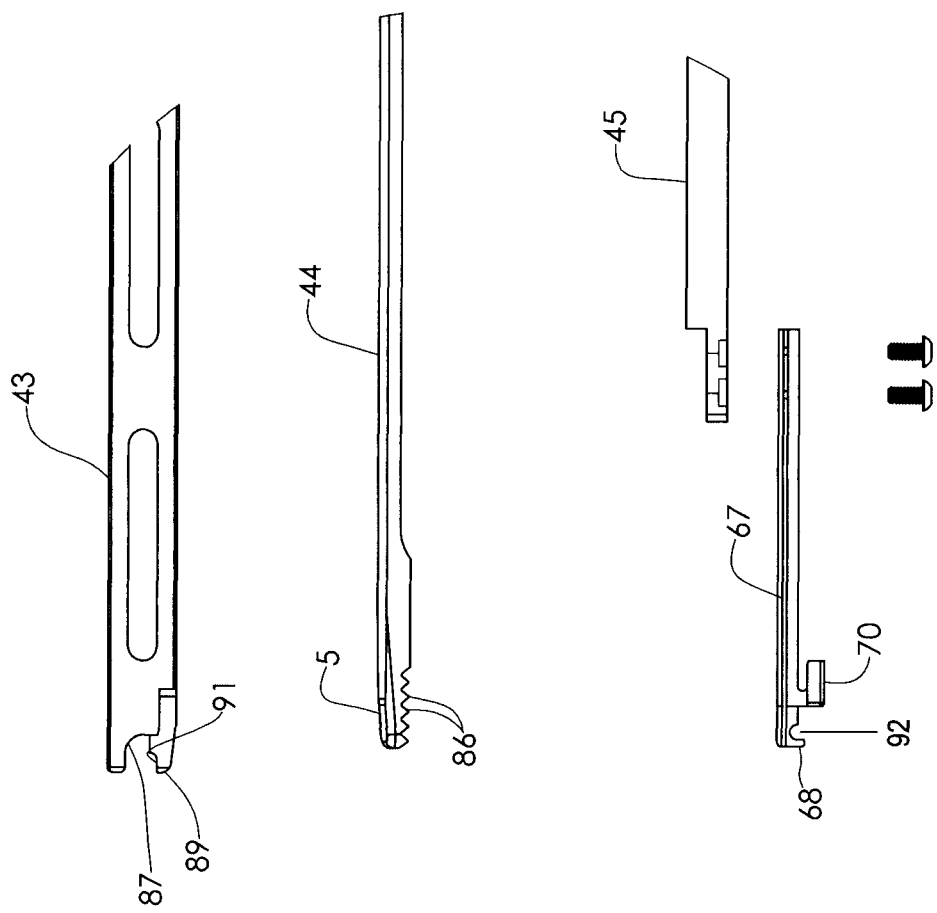

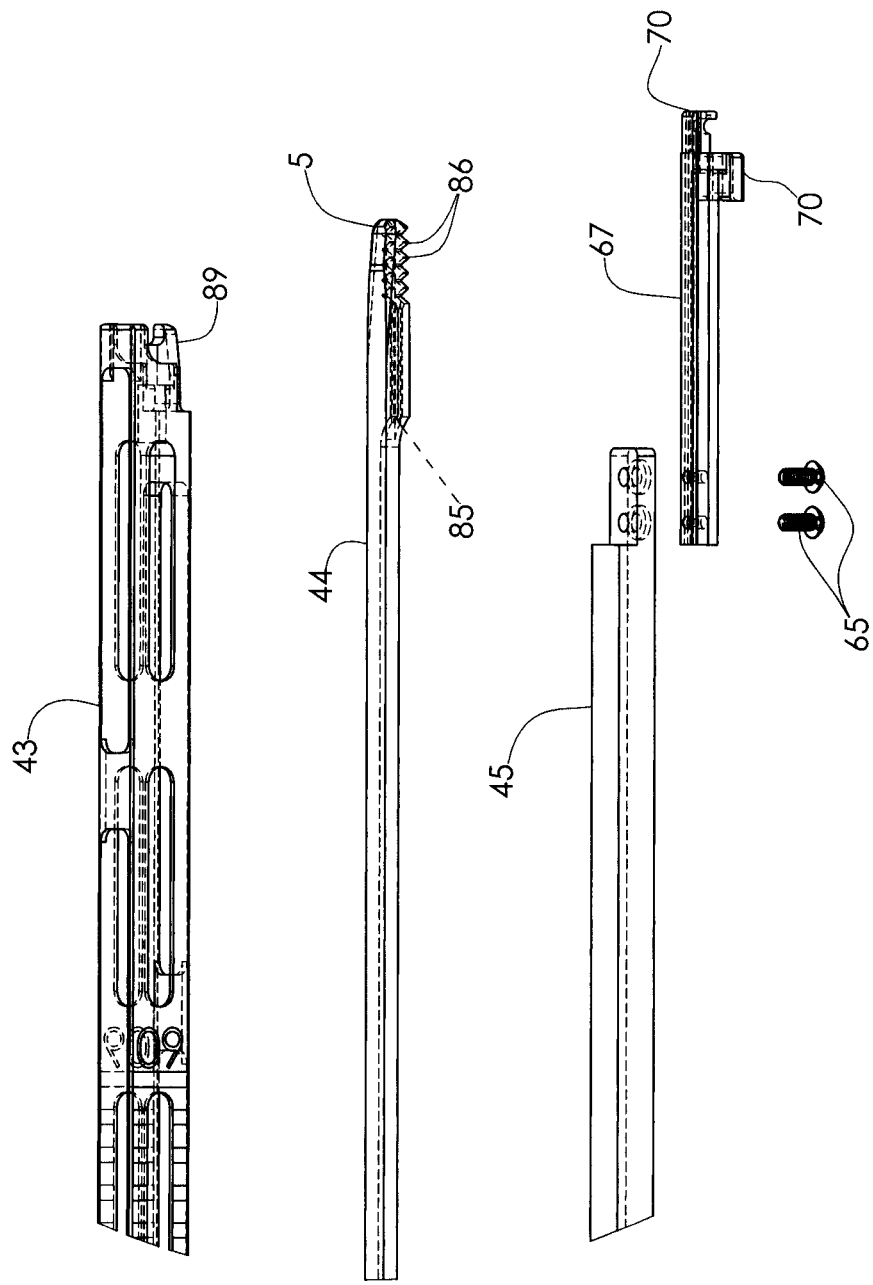

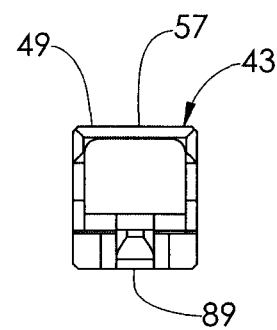
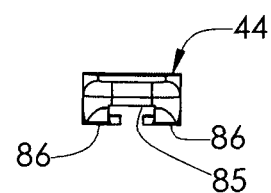
Fig. 9
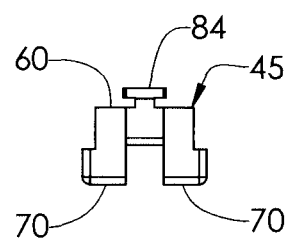

SURGICAL INSTRUMENT FOR IMPLANT INSERTION

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 62/235,085, entitled "Surgical Instrument for Implant Insertion", filed Sep. 30, 2015, and the present invention claims priority as a continuation-in-part of U.S. patent application Ser. No. 15/186,996, entitled "Bone Fixation Rod and Implantation Device for Insertion Thereof", filed Jun. 20, 2016, which is a divisional of U.S. patent application Ser. No. 14/153,768, entitled "Bone Fixation Rod And Implantation Device For Insertion Thereof", filed Jan. 13, 2014, which is now U.S. Pat. No. 9,370,384, which issued on Jun. 21, 2016, which claims priority as a continuation of U.S. patent application Ser. No. 13/107,189, entitled "Bone Fixation Rod and Implantation Device for Insertion Thereof", filed May 13, 2011, which is now U.S. Pat. No. 8,628,535, which issued on Jan. 14, 2014, which claims priority to U.S. Provisional Patent Application No. 61/334,643, entitled "Bone Fixation Rod and Implantation Device for Insertion Thereof", filed May 14, 2010. The present invention is related to U.S. patent application Ser. No. 11/726,865, entitled "Pivotable Interbody Spacer", filed Mar. 22, 2007, which is now U.S. Pat. No. 8,043,293, which issued on Oct. 25, 2011; U.S. patent application Ser. No. 11/856,483, entitled "Pivotable Vertebral Spacer", filed Sep. 17, 2007, which is now U.S. Pat. No. 8,157,845, which issued on Apr. 17, 2012; U.S. patent application Ser. No. 12/051,319, entitled "Pivotable Interbody Spacer System and Method", filed Mar. 19, 2008, which is now U.S. Pat. No. 7,892,239, which issued on Feb. 22, 2011; U.S. patent application Ser. No. 13/006,186, entitled "Pivotable Interbody Spacer System and Method", filed Jan. 13, 2011, which is now U.S. Pat. No. 8,444,650, which issued on May 21, 2013; U.S. Provisional Patent Application No. 61/678,891 entitled "Pivotable Lateral Cage and Method of Insertion", filed Aug. 2, 2012; U.S. patent application Ser. No. 13/958,163, entitled "Pivotable Lateral Cage and Method of Insertion", filed Aug. 2, 2013, which is now U.S. Pat. No. 9,345,587, which issued on May 24, 2016; all of which are now incorporated herein by reference.

FIELD OF THE INVENTION

The instant invention relates to surgical instruments useful in positioning an implant device for insertion in a patient, such as disc repair or bone fixation procedures and methods of use thereof. Such implants include a bone fixation rod, such as a spinal rod used for insertion into a plurality of pedicle screws for alignment purposes during spinal procedures, and a spacer for insertion into an intervertabral disc between two vertebrae.

BACKGROUND OF THE INVENTION

The central nervous system is a vital part of the human physiology that coordinates human activity. It is primarily made up of the brain and the spinal chord. The spinal chord is made up of a bundle of nerve tissue which originates in the brain and branches out to various parts of the body, acting as a conduit to communicate neuronal signals from the brain to the rest of the body, including motor control and sensations. Protecting the spinal chord is the spinal, or vertebral, column. Anatomically, the spinal column is made up of several regions, including the cervical, thoracic, lumbar and sacral regions. The cervical spine is made up of seven vertebrae and functions to support the weight of the head. The thoracic spine is made up of twelve vertebrae and functions to protect the organs located within the chest. Five vertebrae (vertebral bodies) make up the lumbar spine. The lumbar spine contains the largest vertebra and functions as the main weight bearing portion of the spine. Located at the base of the spine are the five fused vertebrae known as the sacrum. The coccyx sits at the base of the spinal column and consists of four fused vertebrae. An intervertabral disc (disc) is located between adjacent vertebrae.

Each of the vertebrae associated with the various spinal chord regions are made up of a vertebral body, a posterior arch, and transverse processes. The vertebral body, often described as having a drum-like shape, is designed to bear weight and withstand compression or loading. In between the vertebral bodies are the intervertebral discs. The intervertebral disc is filled with a soft, gelatinous-like substance which helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebrae.

While most people have fully functional spinal chords, it is not uncommon for individuals to suffer some type of spinal ailment, including spondylolisthesis, scoliosis, spinal fractures, disc rupture and disc herniation. One of the more common disorders associated with the spinal chord is damage to the spinal discs. Damage to the discs results from physical injury, disease, genetic disposition, or as part of the natural aging process. Disc damage often results in intervertebral spacing not being maintained, causing pinching of exiting nerve roots between the discs, resulting in pain. For example, disc herniation is a condition in which the disc substance bulges from the disc space between the two vertebrae bodies. It is the bulging of the disc material which causes impingement on the nerves, manifesting in pain to the patient. For most patients, rest and administration of pain and anti-inflammatory medications alleviates the problem. However, in severe cases, cases which have developed into spinal instability or severe disc degeneration, the damaged disc material between the vertebral bodies is removed and replaced with spinal stabilization implants, such as intervertebral or interspinal inserts. Restoration to the normal disc height allows the pressure on the nerve roots to be relieved.

There are many different approaches taken to alleviate or reduce severe spinal disorders. One surgical procedure commonly used is a spinal fusion technique. Several surgical approaches have been developed over the years, and include the Posterior Lumbar Interbody Fusion (PLIF) procedure which utilizes a posterior approach to access the patient's vertebrae or disc space, the Transforaminal Lumbar Interbody Fusion (TLIF) procedure which utilizes a posterior and lateral approach to access the patient's vertebrae or disc space, and the Anterior Lumbar Interbody Fusion (ALIF) which utilizes an anterior approach to access the patient's vertebrae or disc space. Using any of these surgical procedures, the patient undergoes spinal fusion surgery in which two or more vertebrae are linked or fused together through the use of a bone spacing device and/or use of bone grafts.

The resulting surgery eliminates any movement between the spinal sections which have been fused together.

In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse. Currently available systems for inserting the rods into pedicle screws can be difficult, particularly in light of the fact that surgeons installing these rods often work in narrow surgical fields, as for example, through tubes. This is well known in the art. Once the implant is moved through the access tube in a longitudinal orientation, it needs to be reoriented for attachment to the screws. Reorientation can be difficult when working through a surgical device such as an access tube. Moreover, since patients can vary with respect to their internal anatomy, resulting in varying curvatures of the spine, a surgeon may not always have a linear path or may have anatomical structures that need to be maneuvered around in order to properly insert the surgical rods into the pedicle screw assemblies. In addition to requiring surgical skill, difficulty in placing the rods correctly into the pedicle screws can result in unnecessary increases in the time it takes a surgeon to complete the surgical procedure. Prolonged surgery times increase the risk to the patient. More importantly, improperly aligning the rods and pedicle screw assemblies often results in complications for the patient and can require corrective surgical procedures.

Similar problems are also encountered with other surgical procedures; for example, when implanting an interspinal insert. Once the implant is moved through the tube to the surgical site, it is turned to re-orient it for insertion between two vertebra. Reorientation can be difficult when the surgical tube that provides access has a small cross-sectional area, as the implant needs to be inserted along the tube in a longitudinal orientation. This is true for disc implants as well.

There exists, therefore, a need for an improved surgical implantation instrument that can be used by a surgeon to easily and safely insert an implant device such as a bone fixation rod to a plurality of members of a bone fixation system, such as pedicle screws which have been inserted into various bone structures, or insert an intervertebral insert, particularly when a tube is used to provide access to the surgical site. U.S. Pat. No. 8,157,845, entitled "Pivotable Vertebral Spacer" filed Sep. 17, 2007; U.S. Pat. No. 7,892,239, entitled "Pivotable Interbody Spacer System and Method" filed Mar. 19, 2008; and U.S. Pat. No. 8,444,650 entitled "Pivotable Interbody Spacer System and Method" filed Jan. 13, 2011, disclose an interbody spacer suitable for use with the present tool. U.S. Pat. No. 8,628,535 entitled "Bone Fixation Rod and Implantation Device For Insertion Thereof" filed May 13, 2011, discloses a fixation rod and insertion tool usable in a method to implant the rod. The entirety of these applications is incorporated herein by reference.

DESCRIPTION OF THE PRIOR ART

U.S. Pat. No. 6,530,929 discloses an installation instrument for placement of a brace or rod into pedicle screws. The instrument is mounted to anchors secured to the pedicle screws utilizing extensions coupled to the anchors. The instrument is movable with respect to the anchors to position a brace in a position more proximate the anchors. The brace can be inserted into the pedicle screws and manipulated away from the installation instrument utilizing a thumb screw. However, a disadvantage associated with the installation instrument for placement of a brace or rod into pedicle screws described therein is that the brace can not be rotated about its longitudinal axis.

U.S. Pat. No. 7,188,626 discloses methods and instruments for placing a brace or connecting element into a plurality of anchors or pedicle screws similar to U.S. Pat. No. 6,530,929. Insertion of the connecting elements is accomplished by a linear insertion method, therefore failing to teach a connecting element that cannot be rotated about its longitudinal axis.

U.S. Pat. No. 7,520,879 discloses a device for positioning a connecting element adjacent the spinal column using so called minimally invasive procedures. An inserter instrument guides the connecting element from a location remote from one or more anchors to a location proximate to the one or more anchors. The extensions are mountable to anchors, and the inserter instrument is mountable to the connecting element for positioning the connecting element adjacent the anchors in a so-called minimally invasive procedure. The inserter instrument does not have to be mounted to the anchors or to the anchor extensions, and are operable independently to position the connecting element into the patient along a minimally invasive insertion path from a location remote from the anchor extensions. While the inserter instrument can rotate the connecting element along its longitudinal axis, it can not be repositioned on the connecting element to gradually rotate the connecting element in a given direction. Moreover, it cannot be rotated about an axis normal to its longitudinal axis.

U.S. Publication No. 2007/0078460 discloses a method and instrumentation for performing spinal fixation surgery. A first incision is made through the skin and a passageway is created to the spine. A screw is inserted through the passageway and into a vertebra. The screw has a head portion including a channel. An insertion guide is operably connected to the screw. Additional screws may each be inserted through separate incisions or through the first incision. Insertion guides may be operably connected to a head portion of each screw. A sleeve may be positioned into one insertion guide in a first position to guide a rod through at least one other insertion guide. The sleeve is rotated to a second position to allow the rod to move down the slots of the insertion guides and into the head portion of the screw. Additionally, a holding instrument can be employed to position a rod. Two types of connections between the holding instrument and the rod are described. These connections permit the rotation of the rod about its longitudinal axis, but fail to teach a rod which can be repositioned on the connecting element to gradually rotate the connecting element in a given direction.

U.S. Publication No. 2005/0277934 discloses a so-called minimally invasive spinal fixation system used for spinal arthrodesis or motion preservation spinal repair. The system includes a plurality of pedicle screws and an attachment assembly for connecting the pedicle screws. The attachment assembly includes a connector for attaching to the first screw and second screw, and a removable guide for percutaneously attaching the connector to the first screw and second screw. The removable guide includes a number of different embodiments for connecting the attachment assembly to the connector. A snap type lock is used to secure the attachment to the connector. While this does permit the connector to be repositioned by rotating it about its longitudinal axis, the repositioning can occur at only 90 degree increments. Moreover, it cannot be rotated about an axis normal to the longitudinal axis of the connector.

U.S. Pat. No. 7,892,239, and U.S. Publication Nos. 2007/0225808 and 2008/0009880 describe a system and a method for pivotably inserting an interbody spacer device into a surgical site. The system includes an interbody spacer and an insertion instrument with a pivotable element configured to manipulate an interbody spacer. A plurality of teeth is formed on at least one end of the spacer, and matching teeth are formed on an insertion instrument. An exemplary insertion instrument includes an expandable tip configured to be inserted and mated with a gap within an interbody spacer to aid in selective retention and manipulation of the interbody spacer.

SUMMARY OF THE INVENTION

The present invention provides for a tool usable by a surgeon for orthopedic procedures to move an implant to a surgical site, and when clear of obstruction, rotate the implant by remote action to facilitate the fixing of the implant in the patient at the surgical site, and then remotely release the implant from the tool.

The tool has means for releasably securing an implant at its distal end, and means at the proximal end to remotely effect rotation of the implant relative to the tool from a first insertion orientation and a second installation orientation. The tool has means forming a jaw arrangement operable to capture an axle on the implant and secure the implant to the tool. The opening of the jaw structure allows for securing and release of the implant. Retention and release of the implant are independent of operating the tool for rotation of the implant. The implantation device also provides the surgeon with the ability to maneuver the implant remotely in a non-linear fashion around tissue structures by incrementally changing the rotational position of the implant.

Accordingly, it is a primary objective of the instant invention to provide an improved tool for inserting an implant into a patient.

It is a further objective of the instant invention to provide a tool for angular adjustment of the implant during insertion.

It is yet another objective of the instant invention to provide an implant insertion tool which can lock the implant in rotational position in order to maintain an angular position.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 3A is side view of the surgical tool of FIG. 1, illustrated with an intervertebral implant secured thereto;

FIG. 3B is an enlarged fragmentary view, taken along lines 3B-3B of FIG. 3A, of the distal end of the tool of FIG. 1 having an intervertebral implant device rotated to a first position for movement to the surgical site;

FIG. 4 is an enlarged fragmentary side view of the distal end of the tool of FIG. 1 having an intervertebral implant device rotated to a second position for insertion or after insertion at the surgical site;

FIG. 5 is an enlarged exploded fragmentary side view of the distal end of the tool of FIG. 1 taken along lines 5-5 of FIG. 2 showing details of the structure;

FIG. 6 is an enlarged exploded fragmentary perspective side view of the distal end of the tool of FIG. 1 to show details of the structure;

FIG. 9 is an exploded partial end view of the distal end of the tool;

DETAILED DESCRIPTION OF THE INVENTION

Figure 1:
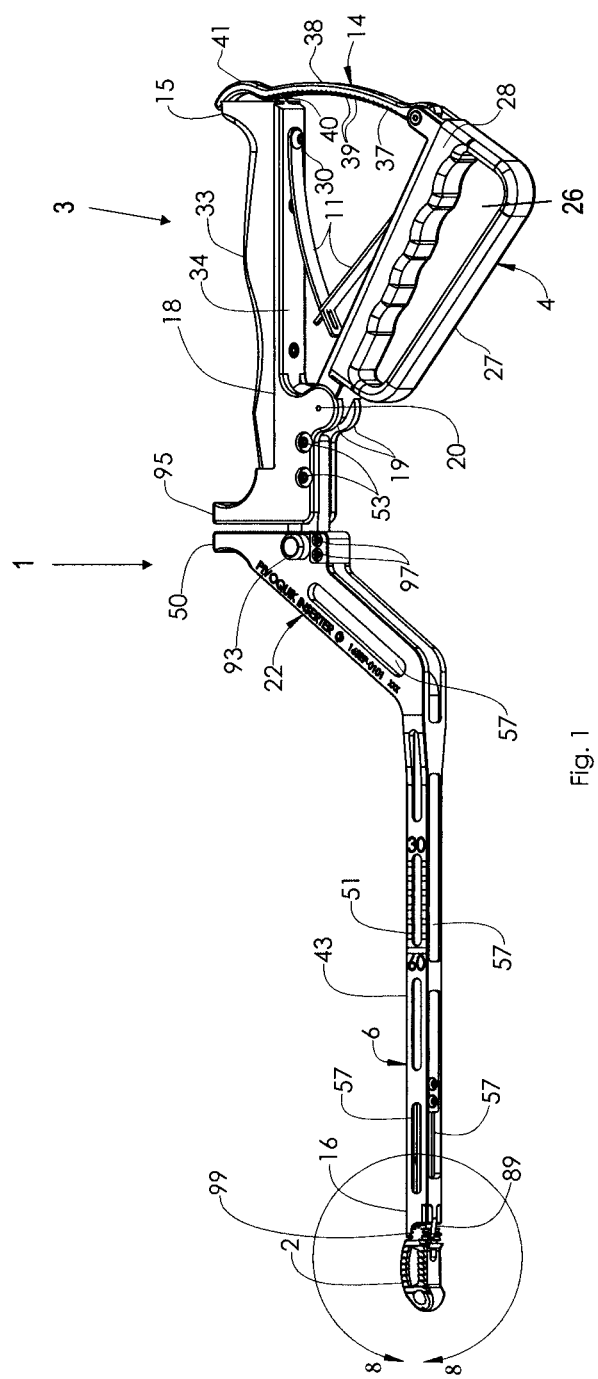
FIG. 1 is a isometric view of a surgical tool for installing an implant.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring generally to FIGS. 1-21. The reference numeral 1 designates a surgical tool adapted for holding an implant device, preferably an orthopedic implant, designated generally as 2, in a secure manner and operable for selectively allowing incremental reorientation of the implant 2 from a longitudinally extending first position as shown in FIG. 1 to a second transverse orientation as seen in FIG. 4 about axis 99. The orientation of the implant 2 as seen in FIG. 1 is for allowing the tool 1 to move the implant through a tube or distractor (not shown) to a surgical site, such as a patient's spine, while the position of the implant 2 as seen in FIG. 4 is for insertion into a desired position in the patient. As seen, the tool 1 includes a handle section 3 having a movable grip 4 for effecting movement of a gear rack 5 (FIG. 4) movably carried by an elongate probe 6 which is secured to the handle 3. In a preferred embodiment, the tool 1 includes biasing means such as leaf springs 11 and lock means 14 which will selectively lock the grip 4 in a selected pivoted position, and thus the implant 2 at any desired rotational position. The tool 1 has a proximal end portion 15 and a distal end portion 16.

The handle section 3 includes a shank 18 that is connected to both the probe 6 and the grip 4. As shown, the grip 4 is pivotally mounted between a pair of ears 19 via a pivot pin 20. In a preferred embodiment, the probe 6 is secured to the shank 18 via a leg portion 22. As shown, the leg portion 22 is positioned at an incline between the shank 18 and a distal end 16 portion of the probe 6. In the illustrated embodiment, the grip 4 is comprised of a D loop portion or handle 23 that can be removably secured to a lever portion 24, as with threaded fasteners 25, such as socket head screws. The handle 23 defines a through opening 26 for receiving therethrough the fingers of the tool operator, such as a surgeon. The handle 23 has spaced runs 27, 28 defining the opening 26 on opposite sides and allows the operator to both positively pull the grip 4 toward the shank 18 and to push the handle 23 away from the shank 18 for a purpose later described, and to effect pivoting movement of the grip 4. The leaf springs 11 are configured to also provide a movement of the handle 23 away from the shank 18 from force applied by the springs 11. As shown, one of the springs 11 is suitably removably secured to the shank 18, and one is suitably removably secured to the handle 23 as with suitable button head or truss head screw fasteners 30. As shown, the shank 18 has a grip portion 33 removably secured to an elongate grip mount member 34 that is preferably in the form of an elongate channel member. Securement can be by suitable threaded fasteners such as socket head screws 35. In the illustrated embodiment, the grip mount 34 is tubular and has a generally rectangular cross section.

Referring to FIGS. 1-3 and 10-18. In the illustrated structure, the lock means 14 includes a latch member 38 pivotally mounted on the lever 24, as at 36, with pivot pin 42 and has a plurality of notches 39 on a surface 37 that is positioned adjacent to a proximal end of the grip mount 34. A suitable catch, such as a detent 40, extends outwardly from the grip mount 34 to selectively engage a surface defining a notch 39 to releasably fix the grip 4 in a preselected pivoted position by engaging a notch 39 on the latch 38. A tab 41 has a portion thereof exposed to assist in releasing the latch 38 from retention and allowing the grip 4 to move.

Referring to FIGS. 1-21. In the illustrated embodiment, the probe 6 includes a plurality of components mounted to one another in a manner for selective relative movement. As shown, the shaft includes components 43, 44 and 45. The component 43, is a guide housing having an offset leg portion 48 (comprising part of the leg 22) and an arm portion 49 extending therefrom. Extending from the leg portion 48 is a lug 50. The guide housing 43 defines a channel 52 extending from the end adjacent the handle section 3 to the distal end 16. Portions of the components 44, 45 are received within the channel 52 as later described. Preferably, the channel 52 has a generally rectangular transverse cross-sectional shape. The guide housing 43 can be provided with indicia 51 to assist the surgeon in knowing the position of the distal end 15 in a surgical tube.

The component 45 is a support member that is suitably secured to the handle section 3 as with fasteners 53 such as button head or truss head screw fasteners. The support member 45 has a leg portion 59 (comprising part of the leg 22) received within the leg 48 and an arm portion 60 received within the arm 49. The guide housing 43 is selectively movable relative to the support member 45 in a longitudinal direction along the length of the arms 49, 60. The guide housing 43 may have suitable perforations 57 through walls thereof to allow viewing inside the channel 52 and to reduce weight. In a preferred embodiment, the cross-sectional shape of the channel 52 and the components 43, 44 and 45 is generally rectangular, which prevents relative rotation between the components.

Figure 2:
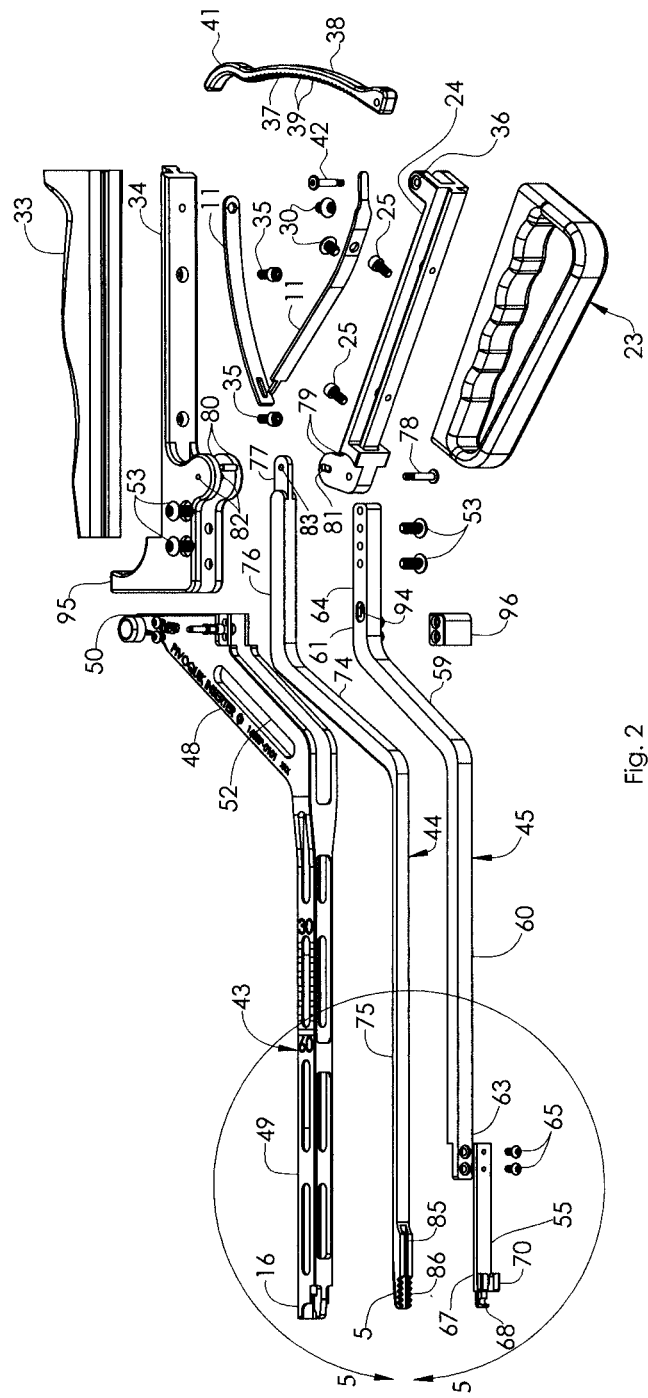
FIG. 2 is an exploded isometric view of the surgical tool of FIG. 1.
Figure 7:
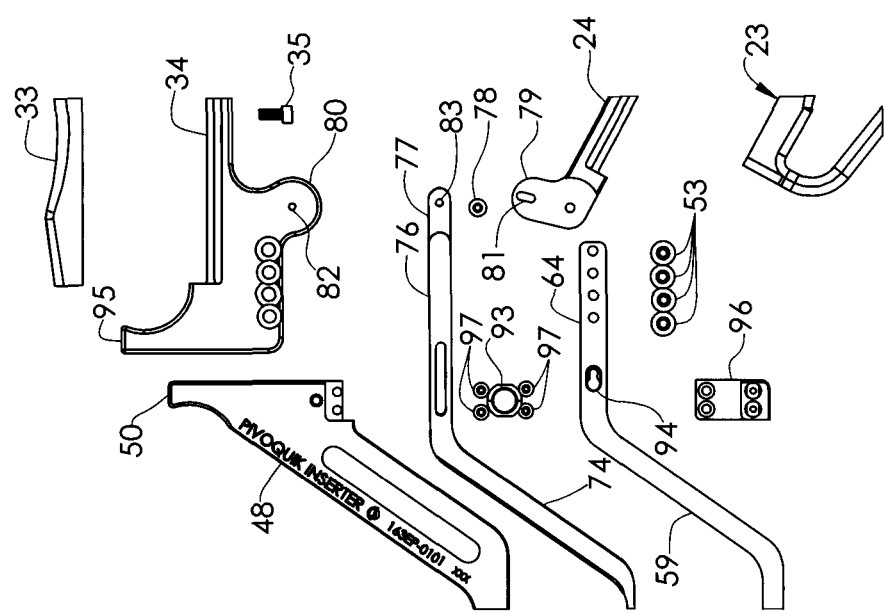
FIG. 7 is an enlarged fragmentary side view of the tool.
Figure 18:
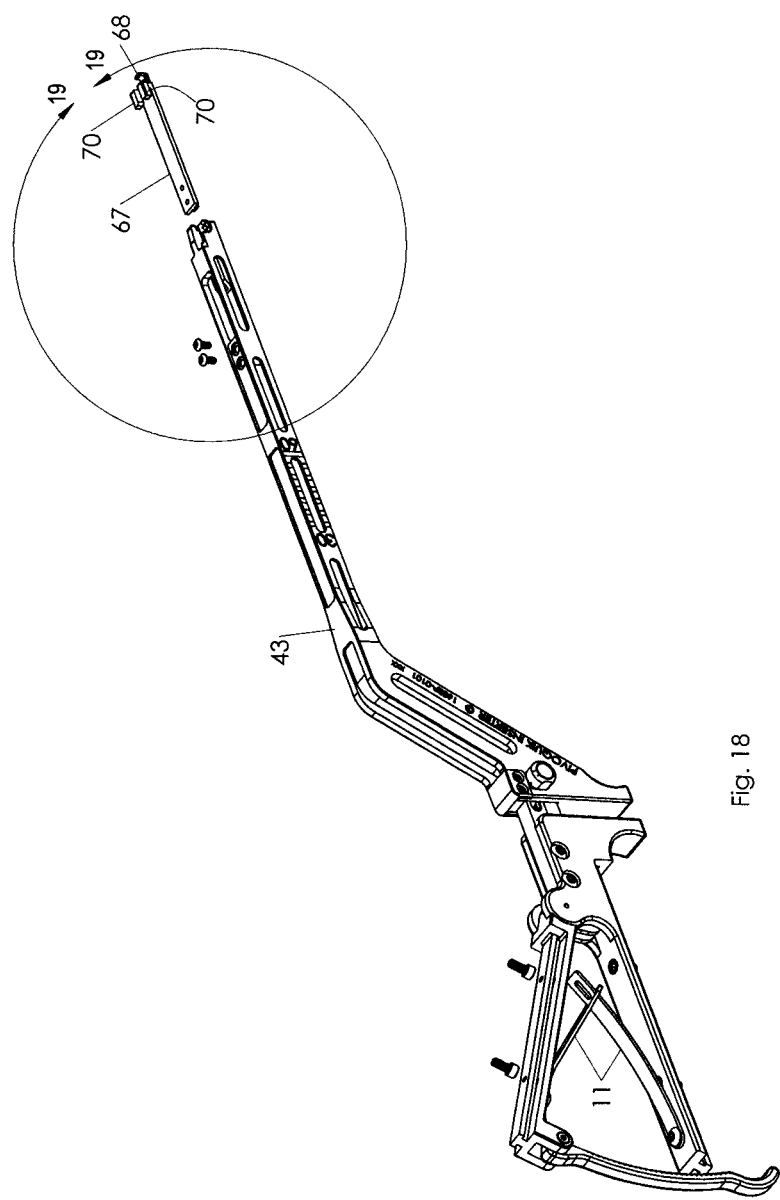
FIG. 18 is a partial isometric and partially exploded view illustrating assembly of the surgical tool.
Figure 19:
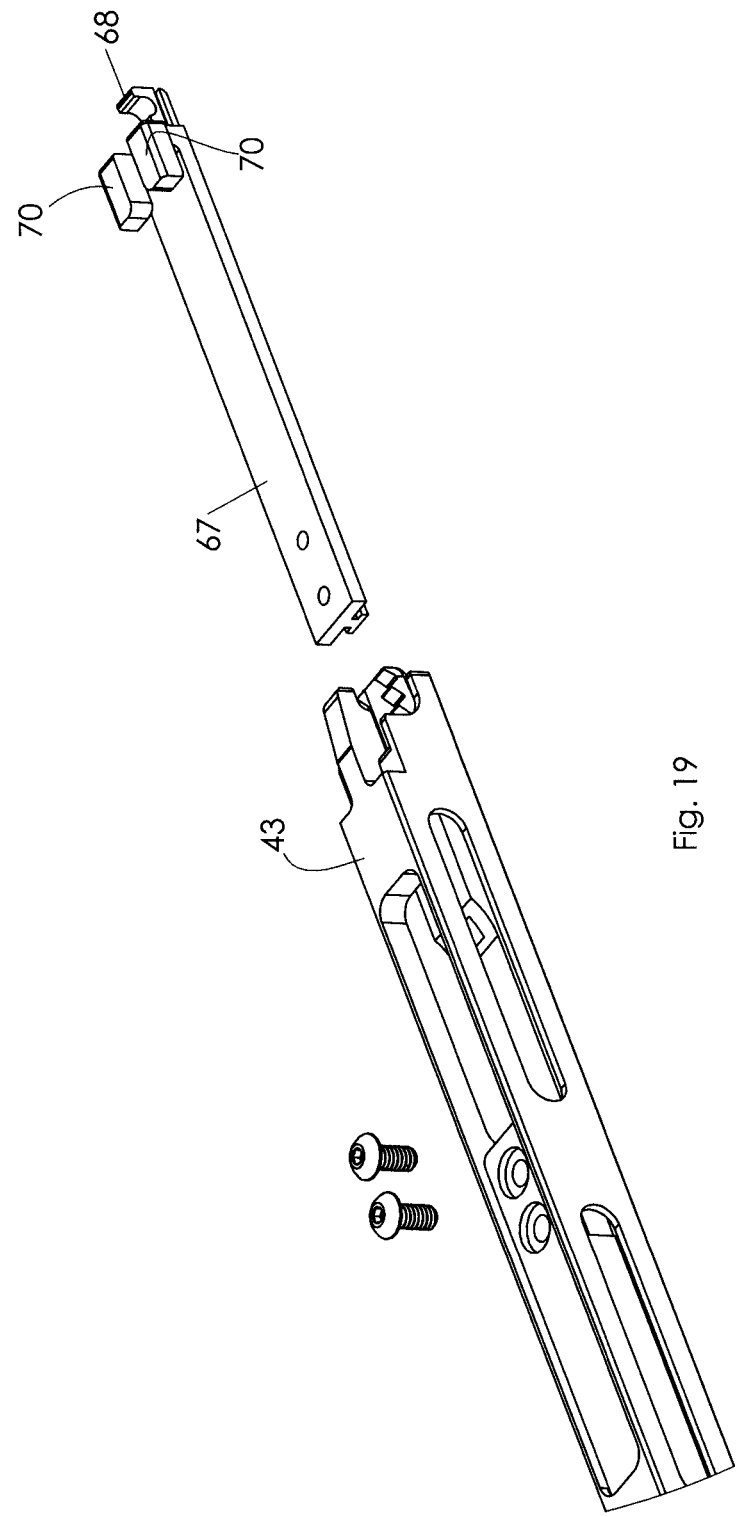
FIG. 19 is an enlarged isometric view taken along lines 19-19 of FIG. 18.
Figure 20:
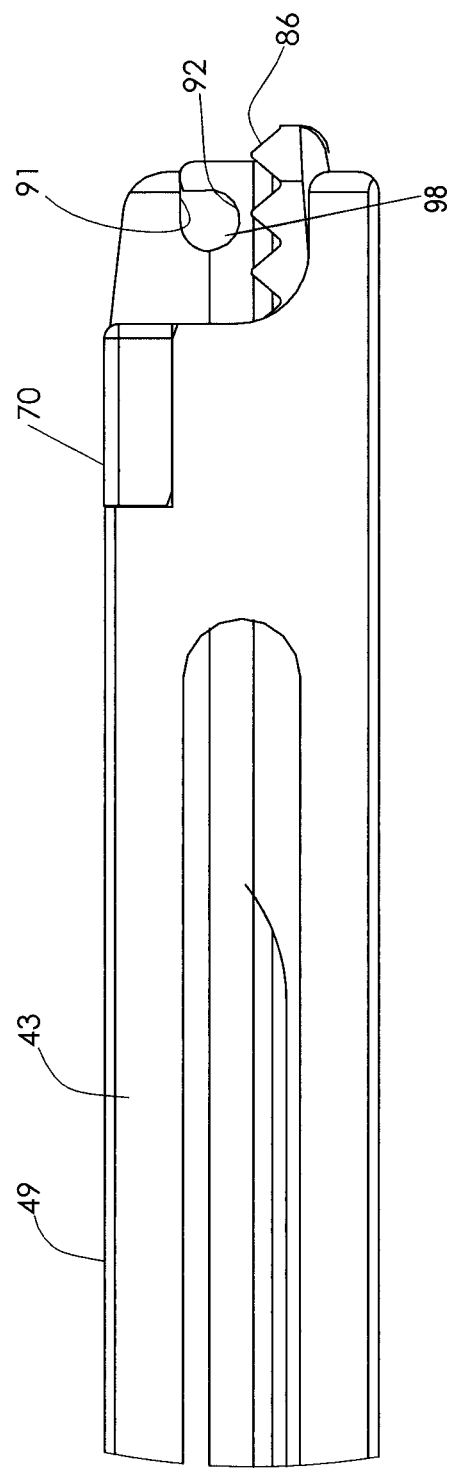
FIG. 20 is a partial side view of the surgical tool.
Figure 21:
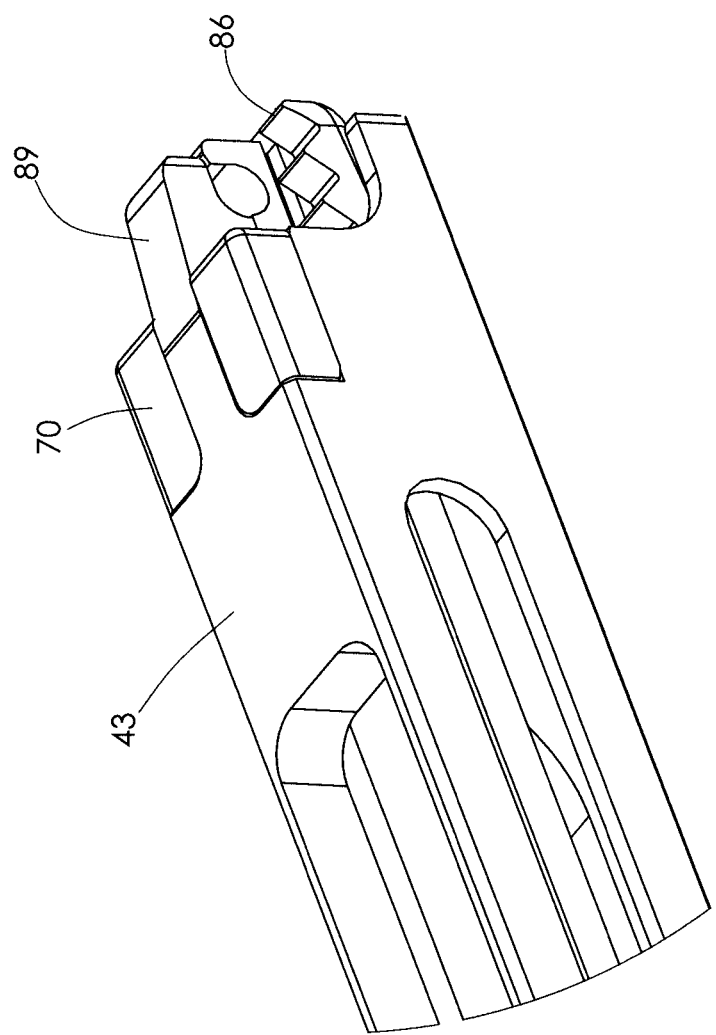
FIG. 21 is a partial isometric view of the surgical tool.

The guide housing 43 and rack carrier 44 are selectively longitudinally movable relative to the handle 3 and support member 45. The support member 45 also includes an extension 61 that is suitably secured to the handle 3, as with suitable fasteners 53 such as button head or truss head screws, as best seen in FIG. 1. As illustrated, the support member 45 preferably has a generally rectangular transverse cross-sectional shape. Preferably, the cross-sectional shape is a solid. The support member 45 has a distal end 63 and a proximal end 64. The proximal end 64 is positioned adjacent the handle 3, and the distal end 63 is positioned adjacent the distal end 16. The support member 45 includes retainer means 55 to help retain an implant removably secured to the tool 1. In a preferred embodiment, the retainer means 55 is removable from the support member 45 as with fasteners 65 such as button head or truss head screws. The retainer means 55 includes a tip 67 that, at its free end, includes a hook 68 that opens generally away from the probe 6. The hook 68 is operable for helping retain an implant 2 releasably attached to the tool 1. In a preferred embodiment, and as best seen in FIGS. 2, 18 and 19, means is provided to releasably fix the support member 45 from retraction movement along the channel 52 of the guide housing 43 during use of the tool 1. The illustrated means includes a pair of laterally spaced apart second hooks 70 which receive a portion of the guide housing 43 in their mouths.

The tool 1 is provided with the rack carrier 44 operably associated with the lever 24 such as with a pivot pin 78 extending through openings or holes 81, 83 in ears 79 on the lever 24 and ears 80 on the grip mount 34. The carrier 44 has a leg section 74 (comprising part of the leg 22) and an arm section 75, both of which preferably have a generally rectangular transverse cross-sectional shape and are solid. The arm 75 and leg 74 are juxtaposed with the arm 60 and leg 59 respectively. An extension 76 extends from the leg 74 into the handle 3. The extensions 61, 76 are preferably also juxtaposed. The leg 74 and extension 76 are positioned at least partially within the channel 52 in the leg 48. A connector 77 is preferably integral with, and extends into, the handle 3 from the extension 76. The lever 24 is connected to the connector 77 in a pivotal manner as with a pivot pin 78 extending through holes 81 in ears 79 of the lever 24, and holes 82 through ears 80 of the grip mount 34, and a hole 83 through the connector 77. As shown, the holes 81 are elongate to allow pivoting of the lever 24. When the lever 24 is moved in either direction, it effects longitudinal movement of the arm 75 within the channel 52 and longitudinally relative to the arms 49, 60. At the distal end of the arm 75, there is provided a rotation means 84 to effect selective rotation of an implant mounted to the tool 1. As shown, the rotation means 84 includes the gear rack 5 having a channel 85 positioned between two rows of gear teeth 86. The gear teeth 86 face the tip 67. As seen in FIG. 9, the channel 85 is T-shaped and receives therein a correspondingly T-shaped slide 84 which is part of the arm 60 of the support member 45 for retained sliding relative longitudinal movement.

Figure 8:
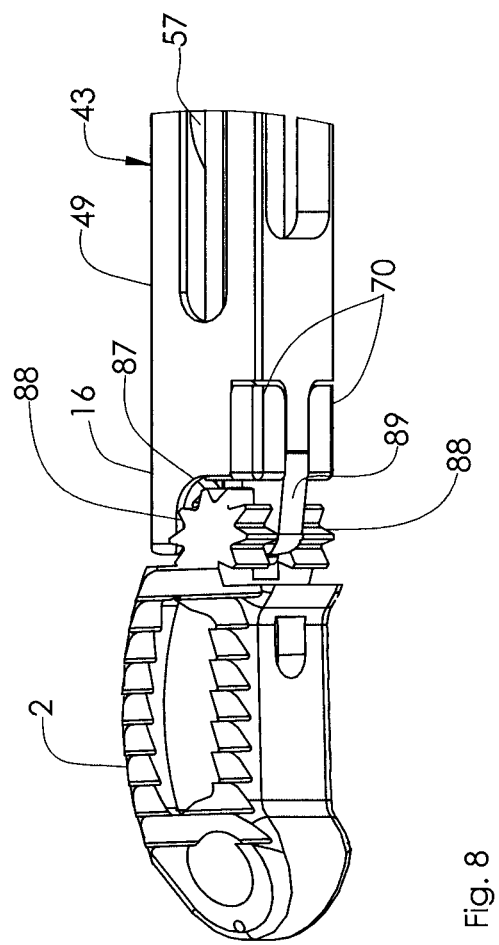
FIG. 8 is an enlarged fragmentary perspective view of the distal end of the tool and implant.
Figure 10:
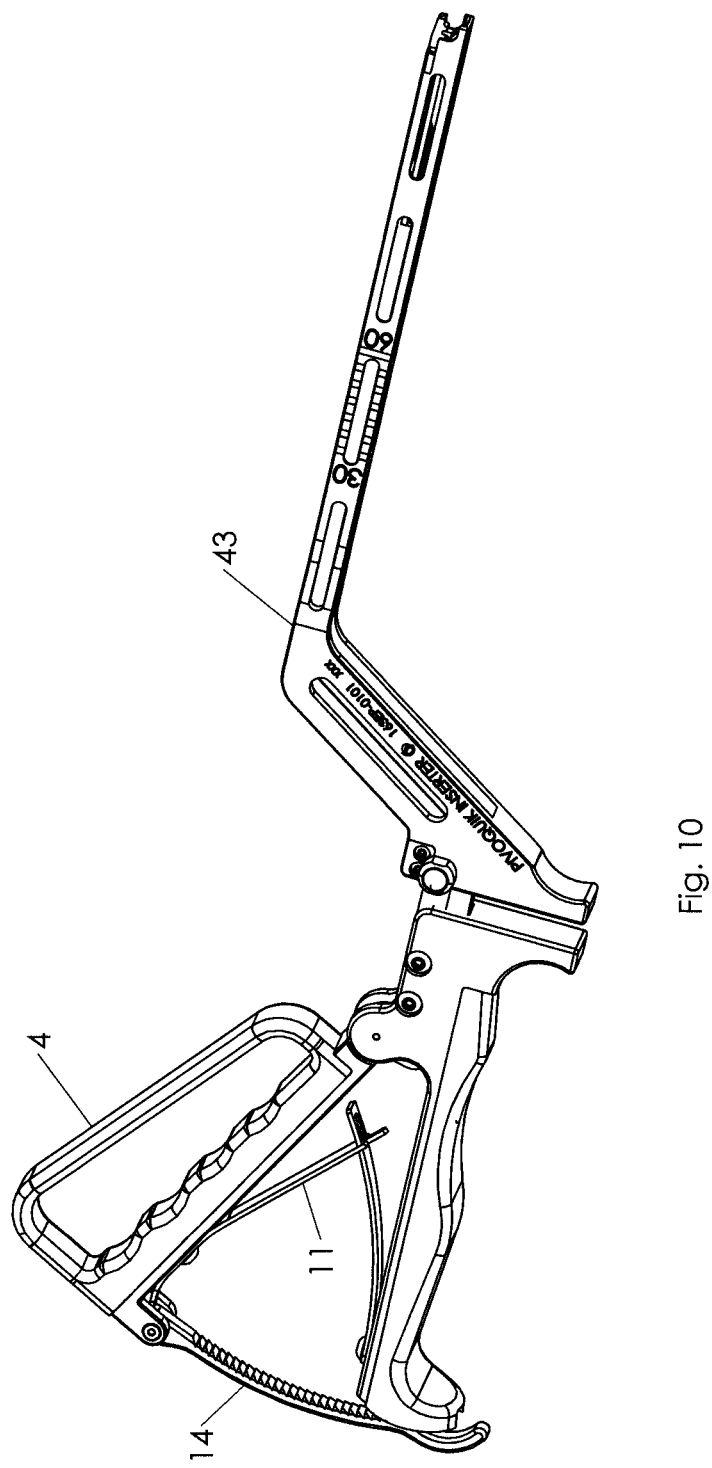
FIG. 10 is an isometric view of a surgical tool for installing an implant.
Figure 11:
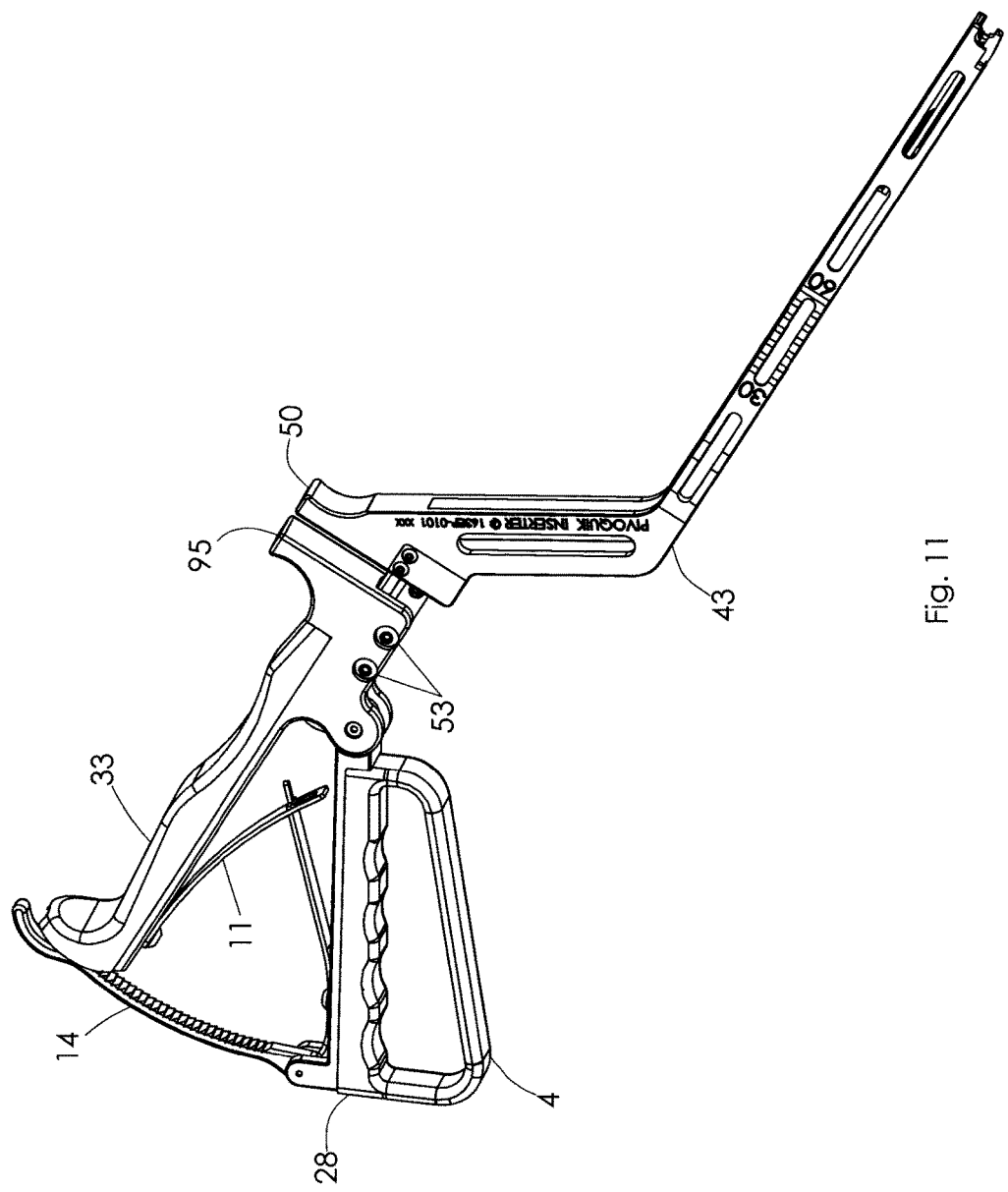
FIG. 11 is an isometric view of a surgical tool for installing an implant.
Figure 12:
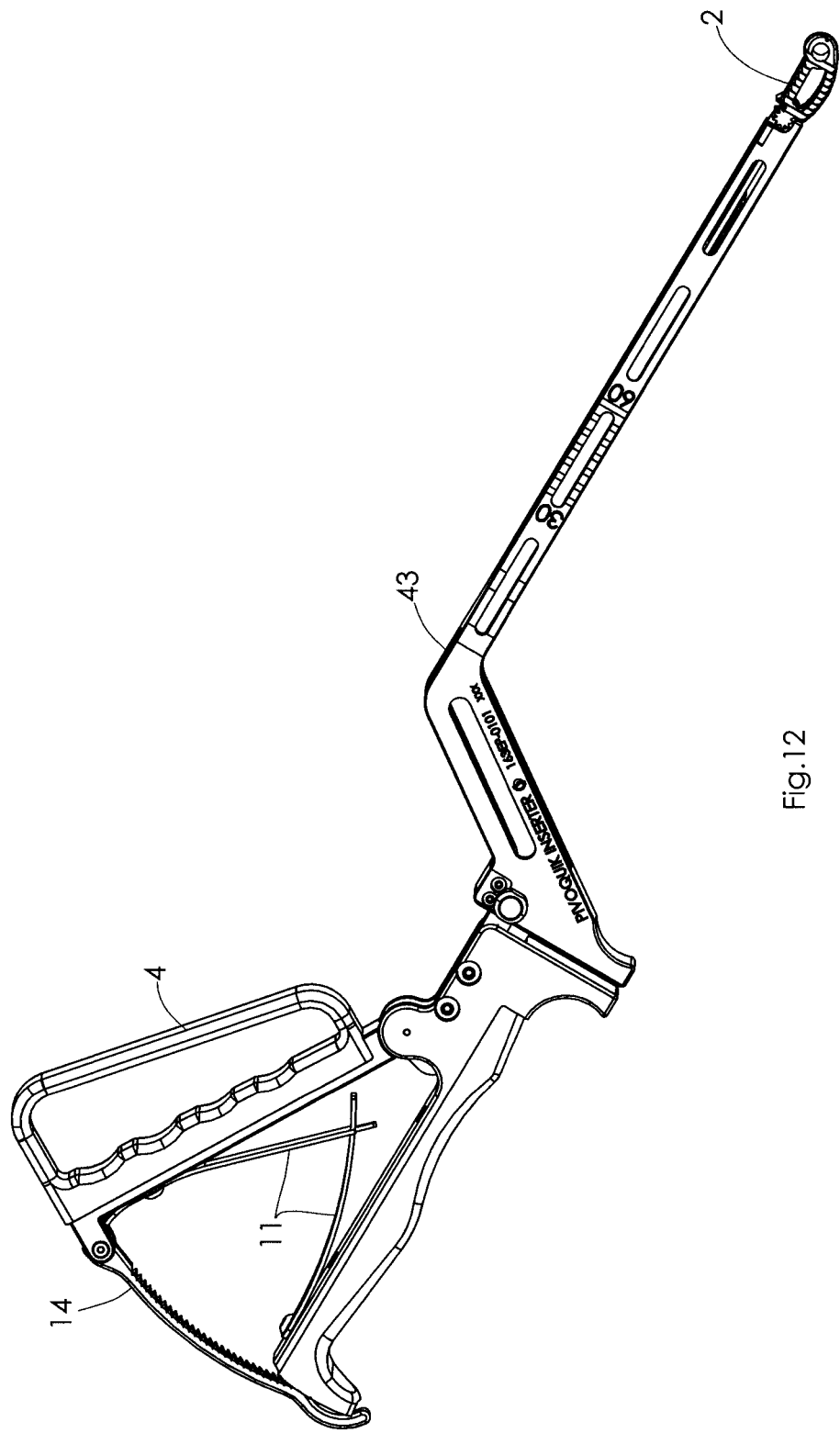
FIG. 12 is an isometric view of a surgical tool illustrated with an intervertebral implant in a first position.
Figure 13:
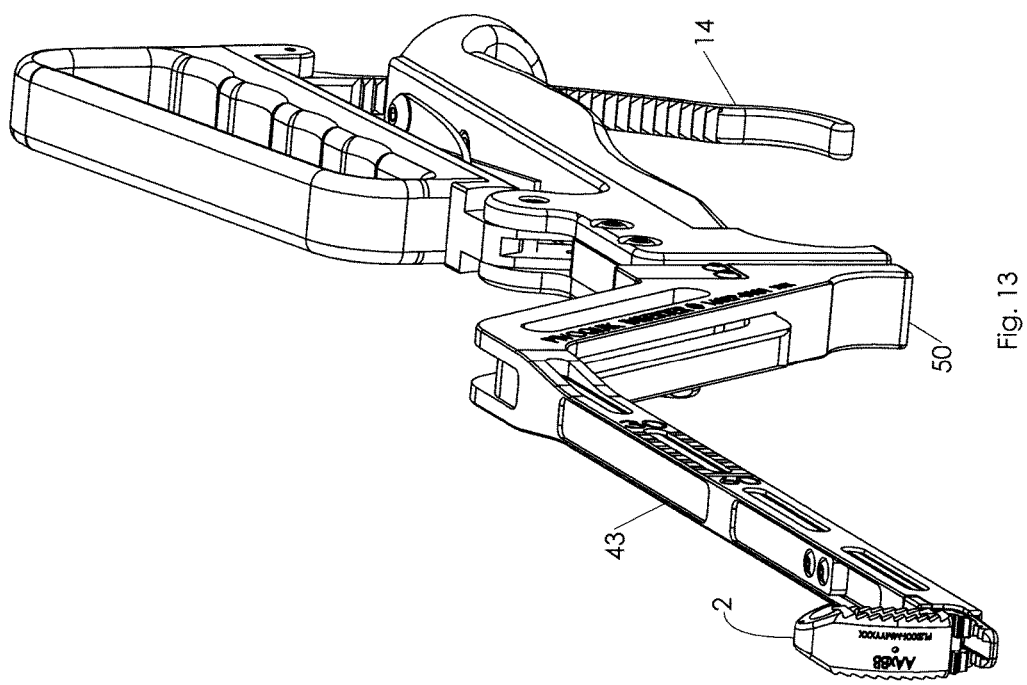
FIG. 13 is an isometric view of a surgical tool illustrated with an intervertebral implant in a second position.
Figure 14:
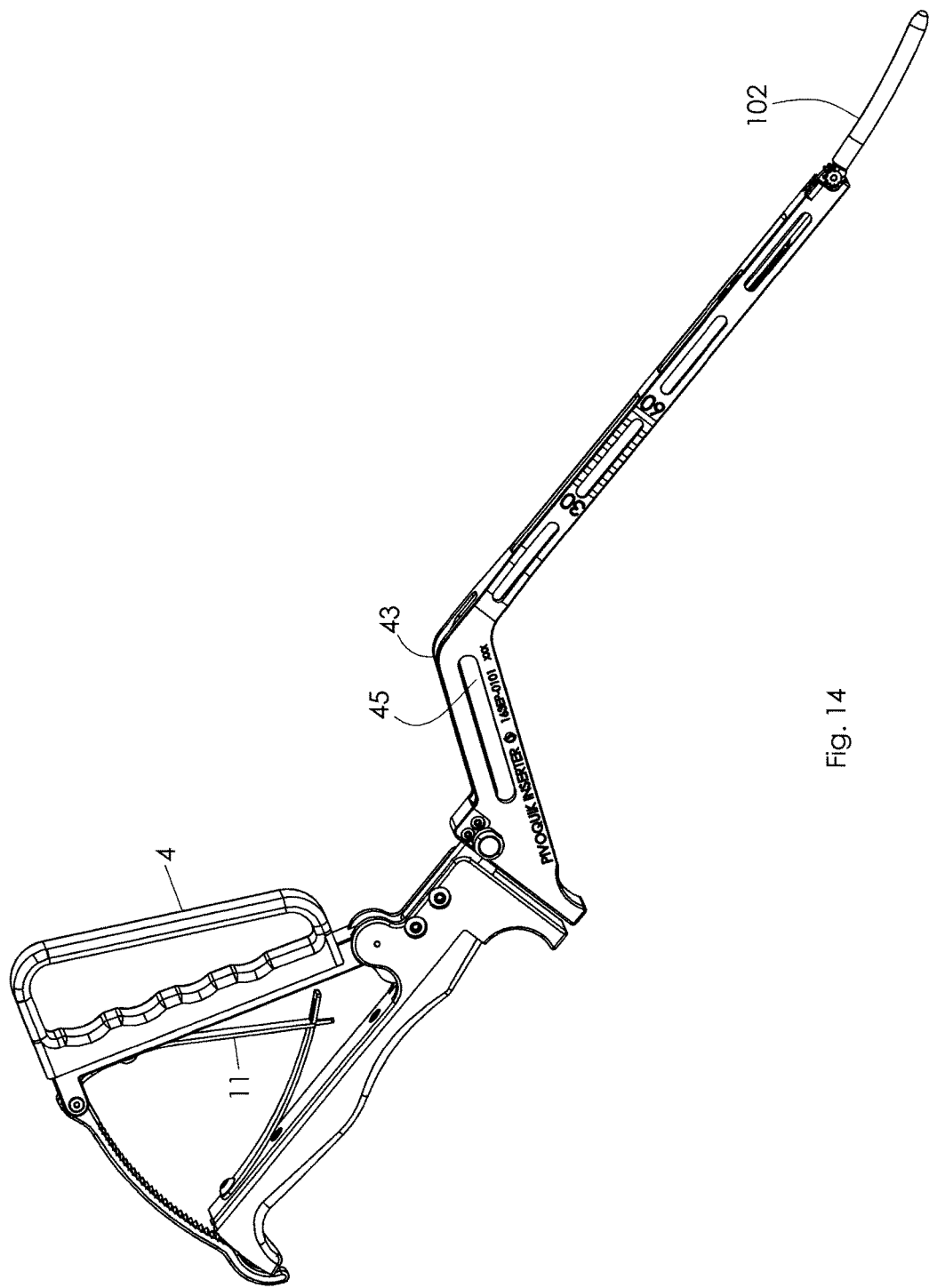
FIG. 14 is an isometric view of a surgical tool illustrated with a rod, in a first position, for connecting spinal implants.
Figure 15:
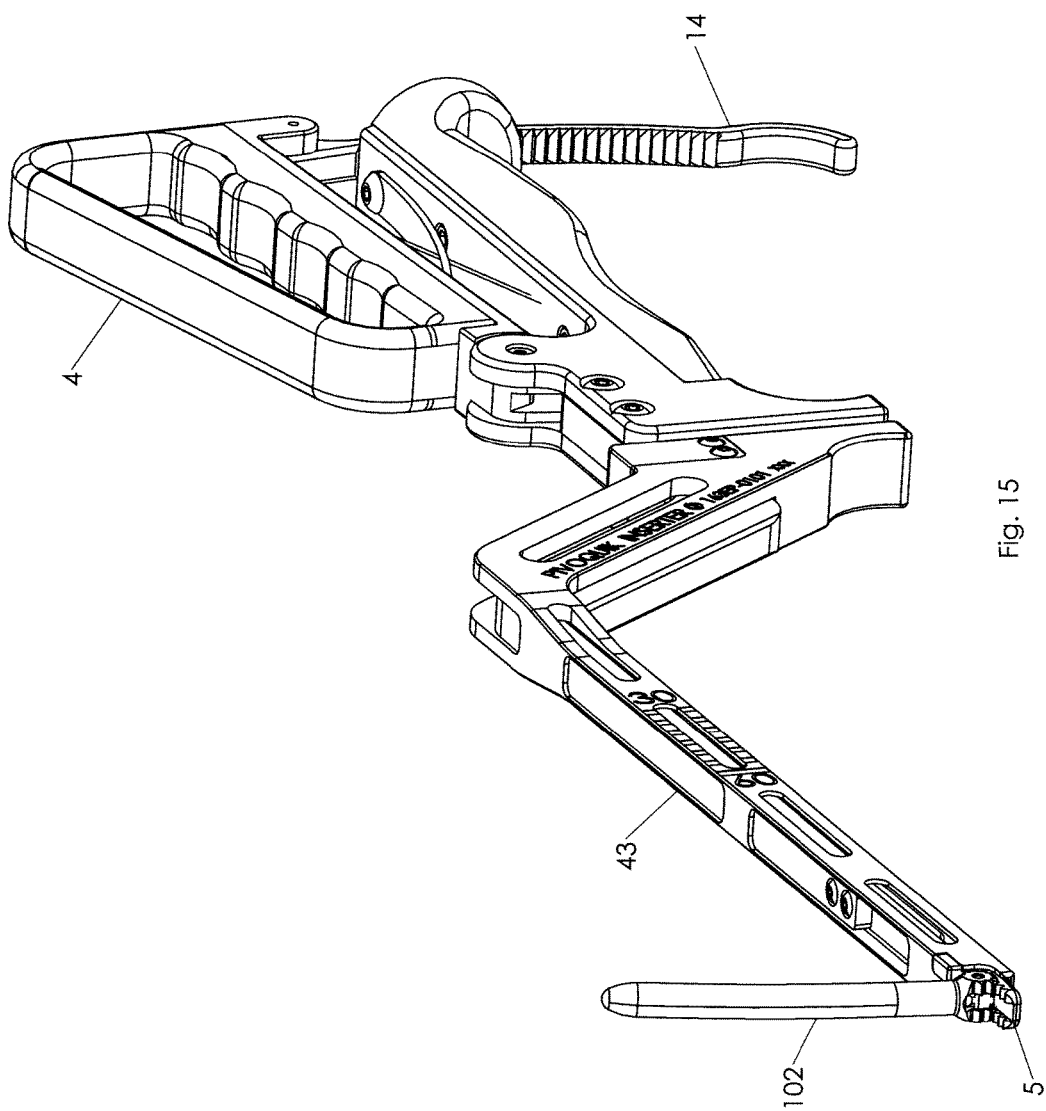
FIG. 15 is an isometric view of a surgical tool illustrated with a rod, in a second position, for connecting spinal implants.
Figure 16:
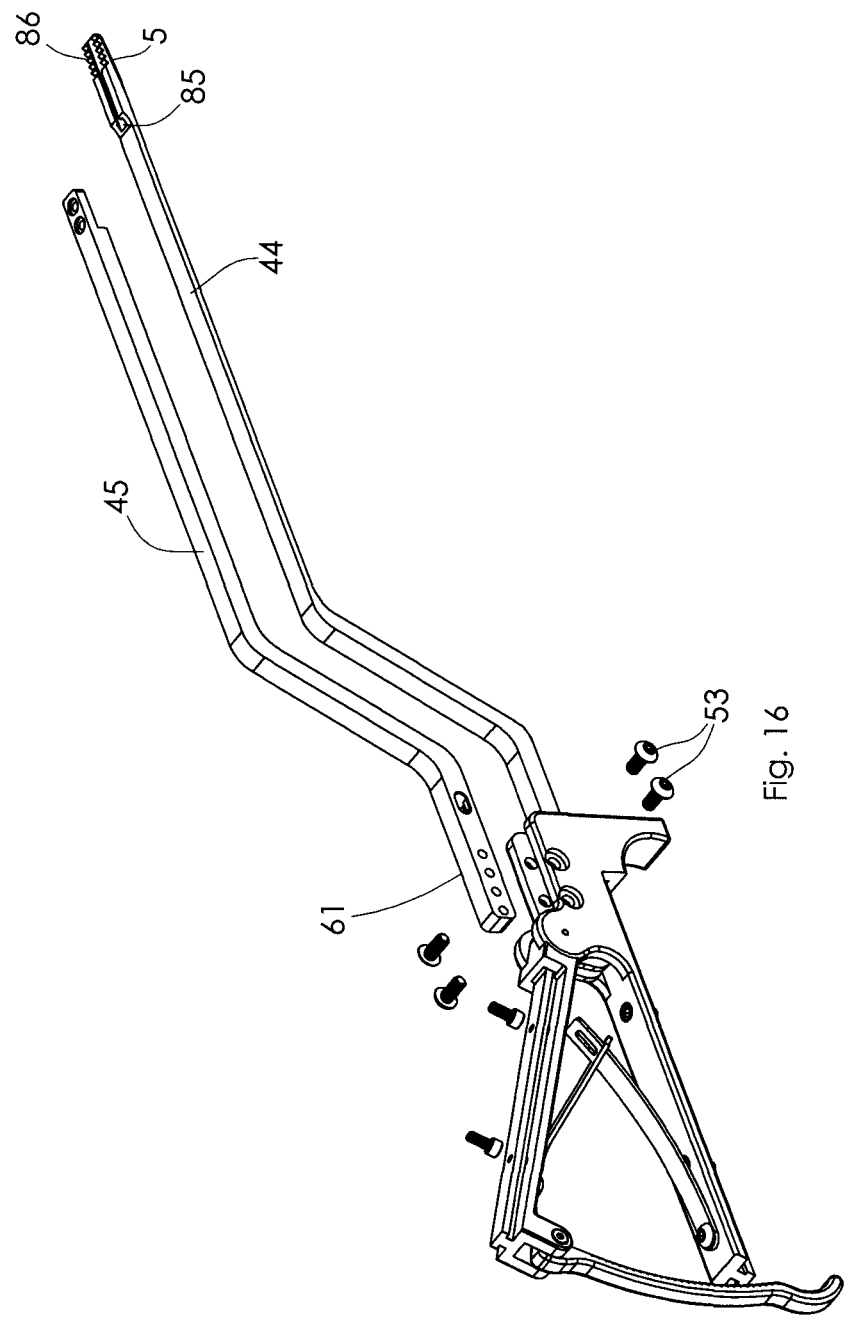
FIG. 16 is a partial isometric and partially exploded view illustrating assembly of the surgical tool.
Figure 17:
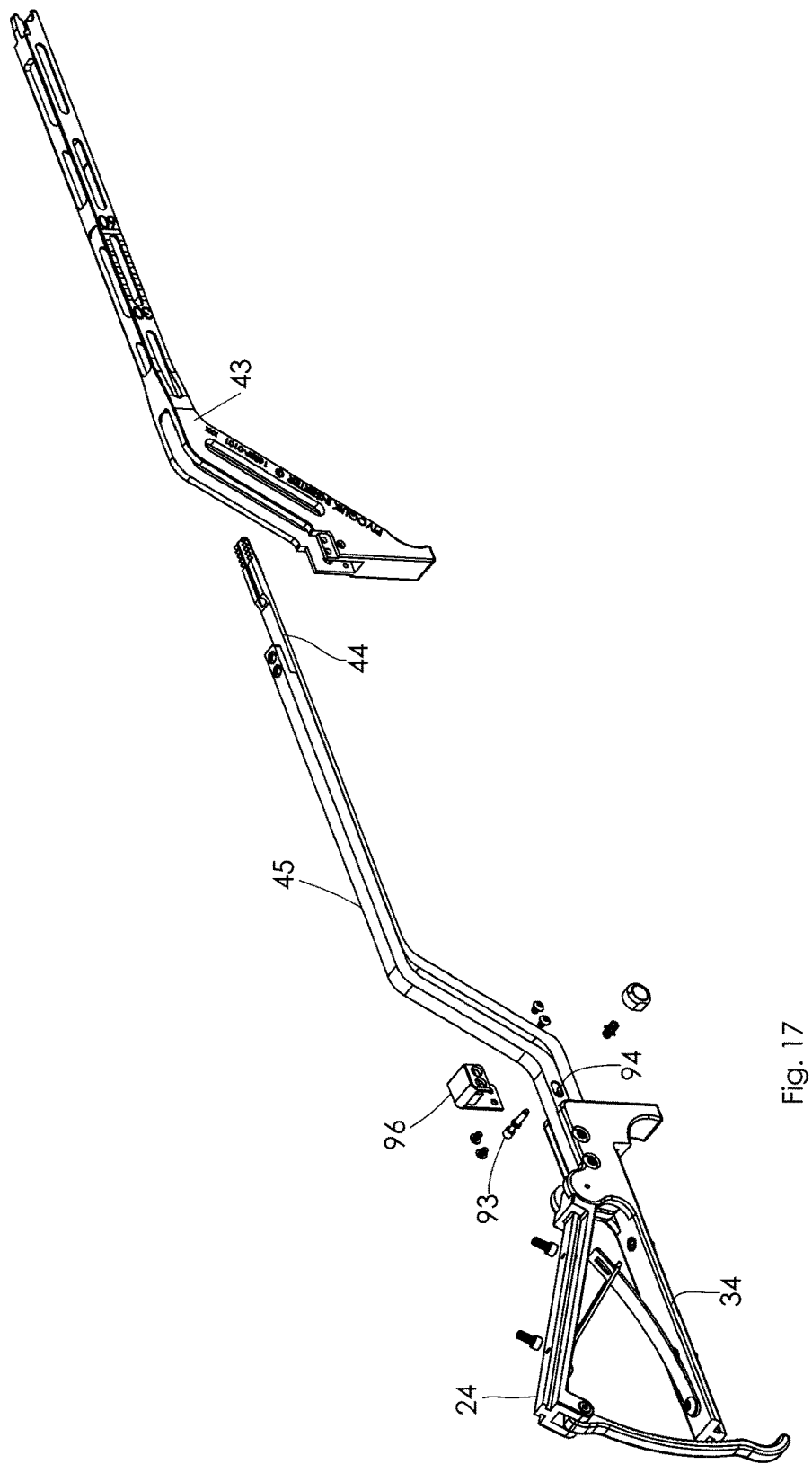
FIG. 17 is a partial isometric and partially exploded view illustrating assembly of the surgical tool.

As best seen in FIG. 8, the distal end 16 of the arm 49 has notches 87 to receive a gear section 88 of the implant 2 in the provided clearance for rotation. The arm 49 also has an implant support finger 89 positioned at its distal end for engaging an axle portion 90 (shown hidden in FIG. 4) positioned between two gear sections 86 of the implant 2. As shown, the finger 89 fits between the two hooks 70 and has a notch 91 (FIG. 5, 20). The finger 89 has a portion configured and positioned to retain the implant 2 removably mounted to the tool 1, and a portion of which prevents the arm 49 from moving past the axle 90 when the arm 49 is being moved relative to the arm 60 for loading and releasing an implant 2.

In the illustrated embodiment, the guide housing 43, rack carrier 44 and support member 45 are configured to prevent relative rotation therebetween while allowing relative longitudinal movement therebetween. In particular, the rack carrier 44 is movable relative to the guide housing 43 and support member 45 by movement of the lever 24. The use of the D loop handle 23 permits the user to positively move the rack carrier 44 longitudinally in two directions. When the gear rack 5 moves in a direction from the proximal end 15 to the distal end 16, the implant 2 will rotate to a counterclockwise position as seen in FIG. 4. When the gear rack 5 moves in the direction from the distal end 16 toward the proximal end 15, the implant 2 will rotate to a clockwise position as seen in FIG. 3. In its initial position for movement to the surgical site, the implant 2 has its longitudinal axis generally parallel to the longitudinal axis of the probe 6 for insertion through a surgical tube. Once in the surgical site and clear of the surgical tube, the implant 2 can be rotated for insertion into the patient and then released from the tool 1 in a manner described below. In a preferred embodiment, the tool 1 has the support member 45 affixed to the handle section 3 in a manner to be immovable relative thereto through the use of the fasteners 53. The rack carrier 44 can move relative to the handle 3 and the support 45 via movement of the lever 24. In a preferred embodiment, movement of the lever 24 toward the grip portion 33 will move the support member 45, and hence the gear rack 5, to an extended position. Movement of the lever 24 away from the grip portion 33 will move the rack carrier 44 and the gear rack 5 to a retracted position. During these latter described movements of the rack carrier 44, the guide housing 43 remains stationary relative to the support member 45.

The implant 2 is releasably mounted to the tool 1 for movement by the gear rack 5 as seen in FIGS. 3, 4. As best seen in FIGS. 1, 3B and 12-15, the implant 2, 102 is secured to the tool 1 adjacent its distal end 16. The implant 2, 102 is provided with the axle 90 which is selectively captured by the hook 68 and finger 89. To release the implant 2, 102 from securement to the tool 1, the guide housing 43 is moved relative to the handle 3 and the support member 45. This in turn moves the finger 89 relative to the hook 68 to provide a passage 92 for the axle 90 to move into and out of the throat 98 of the hook 68. This movement by the operator can be facilitated by use of the lug 50 on the housing 43 and a lug 95 on the handle 3. The finger 89 and hook 68 form jaw means operable to retain the axle 90 in the throat 98 of the hook 68, allowing the implant 2, 102 to be selectively rotated by movement of the lever 24 and gear rack 5. The lugs 50, 95 provide operator finger engaging means. By retracting the finger 89 toward the handle 3 through movement of the guide housing 43 toward the distal end 16, the passage 92 is formed, allowing insertion or removal of the implant 2, 102. By moving the finger 89 in the opposite direction, the passage 92 is closed and closes the throat 98 of the hook 68, securing the implant 2, 102 in position. Preferably, the implant 2, 102 is positioned in a longitudinal orientation relative to the longitudinal axis of the probe 6 for insertion into a surgical tube and the patient. Once in position outside of the surgical tube, the lever 24 can be moved to rotate the implant 2, 102 by moving the gear rack 5 in a direction from the proximal end 15 to the distal end 16 as described above. The implant may be an intervertebral implant 2 or it may be a connecting implant, such as a connecting rod 102 or any other implant that can utilize the axle and gear to facilitate rotation of the implant without departing from the scope of the invention.

Suitable means is provided for fixing the guide housing 43 in selective non-moving relationship to the support member 45, while also allowing movement between the guide housing 43 and support member 45. In the illustrated structure in FIGS. 1 and 17, a pin 93 is positioned for extending through a slot 94 that extends through the proximal end 64 of the support member 45. The pin 93 may be either moved laterally such that a portion of the pin may freely move within the slot 94, or the slot 94 can be figured as, for example, in a FIG. 8 such that the pin can pass through a central reduced size portion of the slot 94, but only with applied force. The pin 93 can be mounted to the guide housing 43 via a mounting block 96 that is suitably secured to the guide housing 43 as with screw fasteners 97 such as button head or truss head screws.

In a preferred embodiment, the components of the tool 1 are made of metal alloys suitable for surgery, such as stainless steel and/or titanium. These provide strength, wear resistance and the ability to be sterilized and reused. The tool 1 can also be partially or completely disassembled to assist in cleaning, maintenance and repair. In order to be used in surgical access tubes, the sides of the arm 49 of the probe 6 is less than about ½ inch in width, and preferably less than about ⅜ inch.

In operation, the tool 1 has an implant 2, 102 removably secured thereto. The passage 92 is opened by movement of the arm 49 toward the proximal end 15. The implant 2, 102 has the axle 90 inserted into the throat 98 of the hook 68 and positioned rotatably as desired, but preferably longitudinally as seen in FIG. 1. The arm 49 is then moved so that the finger 89 closes the passage 92 and captures the axle 90 in the throat of the hook 68. The probe 6 and implant 2, 102 are moved to the surgical sight, such as through a surgical tube if present. Once the implant 2, 102 is at the location for installation, the implant 2, 102 is rotated about its axle 90 by movement of the lever 24 and the gear rack 5 to the desired rotational position, such as that seen in FIG. 4. The implant 2, 102 is installed and then released from the tool 1. The tool 1 is then removed from the patient and surgical sight. The lock means 14 are operable to fix the implant 2, 102 at any desired rotational position.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical tool for traversing a pathway with a removably secured implant, the tool comprising:
    a probe having jaw operable to releasably retain an implant at a distal end of the probe, said probe having a guide housing operable to selectively effect movement of a portion of the jaw to selectively provide a passage for receiving a portion of said implant therethrough and releasable rotatably mounting of said implant to said probe, said probe including a rack carrier having a linear motion gear rack operably associated therewith, said linear motion gear rack being operable to engage a gear tooth on said implant; and
    a handle having a lever pivotally mounted thereto, said lever being operably associated with said rack carrier to effect selective movement of said linear motion gear rack relative to said implant gear tooth and rotation of said implant.

2. The surgical tool for traversing a pathway with a removably secured implant of claim 1 wherein rotation of said implant is selective and incremental.

3. The surgical tool for traversing a pathway with a removably secured implant of claim 1 wherein rotation of said implant is bi-directional about a single axis.

4. The surgical tool for traversing a pathway with a removably secured implant of claim 1 wherein said lever includes a lock for selectively locking said lever in a selected pivoted position whereby said implant is locked at a rotational position.

5. The surgical tool for traversing a pathway with a removably secured implant of claim 4 wherein said lock includes a latch member pivotally mounted to said lever and includes a plurality of notches on a surface thereof, a detent is positioned to selectively engage at least one said notch to releasably fix said lever and said implant in a preselected pivoted position.

6. The surgical tool for traversing a pathway with a removably secured implant of claim 4 wherein said lever includes a biasing means for providing resistance to movement of said lever in a first direction, said biasing means having sufficient force to move said lever in a second direction when said lock is disengaged.

7. The surgical tool for traversing a pathway with a removably secured implant of claim 1 wherein said probe includes a plurality of components mounted to one another in a manner for selective relative movement including a support member fixedly secured to said handle, a rack carrier secured to said lever, said support member extending the length of said probe and providing a linear guide for moving components.

8. The surgical tool for traversing a pathway with a removably secured implant of claim 7 wherein said rack carrier extends adjacent to said support member.

9. The surgical tool for traversing a pathway with a removably secured implant of claim 8 including a guide housing, said guide housing being a tubular member extending around said support member and said rack carrier.

10. The surgical tool for traversing a pathway with a removably secured implant of claim 9 wherein said guide housing and said rack carrier each include indicia for indicating the rotational position of said implant.

11. The surgical tool for traversing a pathway with a removably secured implant of claim 9 wherein said implant includes an axle and at least one said gear tooth, whereby said axle is captured by a portion of said guide housing and a hook secured to said support member so that said at least one gear tooth engages said linear motion gear rack.

12. The surgical tool for traversing a pathway with a removably secured implant of claim 1 wherein said implant is an intervertebral implant.

13. The surgical tool for traversing a pathway with a removably secured implant of claim 1 wherein said implant is a connecting element for connecting at least two spinal implants.

14. The surgical tool for traversing a pathway with a removably secured implant of claim 13 wherein said connecting element is a spinal rod.

15. A method of installing an implant in a patient, the method comprising:
    removably mounting an implant on a distal end of a probe in a manner for selective rotation of the implant relative to the probe, said implant having a gear portion and an axle portion, said implant being positioned a first rotational position relative to the probe;
    positioning the implant at a desired rotational position relative to the probe;
    moving the implant to a surgical sight;
    rotating the implant on its axle by moving a linear motion gear rack along a longitudinal axis of said probe, said linear motion gear rack engaged with the gear to rotate the gear to a second rotational position relative to the probe;
    installing the implant in the patient; and
    releasing the implant from the probe.

16. A surgical tool for traversing a pathway with a removably secured implant, the tool comprising:
    a probe having jaw operable to releasably retain an implant at a distal end of the probe, said probe having a guide housing operable to selectively effect movement of a portion of the jaw to selectively provide a passage for receiving a portion of said implant therethrough and releasable rotatably mounting of said implant to said probe, said probe including a rack carrier, a guide housing, said guide housing being a tubular member extending around said support member, said rack carrier having a gear rack operably associated therewith, said gear rack being operable to engage a gear tooth on said implant; and
    a handle including a support member fixedly secured to said handle, said support member extending the length of said probe and providing a linear guide for moving components therein, a lever pivotally mounted to said handle, a rack carrier secured to said lever, said rack carrier extending adjacent to said support member, said lever being operably associated with said rack carrier to effect selective movement of said gear rack relative to said implant gear tooth and rotation of said implant.

* * * * *